United States Patent [19]

Nordenstroöm

[11] Patent Number: 4,919,138
[45] Date of Patent: Apr. 24, 1990

[54] METHOD AND APPARATUS FOR SUPPLYING ELECTRIC ENERGY TO BIOLOGICAL TISSUE FOR SIMULATING THE PHYSIOLOGICAL HEALING PROCESS

[76] Inventor: Björn Nordenstroöm, Barrtorpsvägen 9, S-144 00 Rönninge, Sweden

[21] Appl. No.: 272,646

[22] Filed: Nov. 14, 1988

[30] Foreign Application Priority Data

Nov. 13, 1987 [SE] Sweden .................................. 8704456

[51] Int. Cl.$^5$ ............................................... A61N 1/00
[52] U.S. Cl. .................................................... 128/421
[58] Field of Search ............................ 600/13, 14, 15; 128/419 F, 419 R, 421

[56] References Cited

U.S. PATENT DOCUMENTS

| | | | |
|---|---|---|---|
| 3,963,030 | 6/1976 | Newton | 128/303.17 |
| 4,019,510 | 4/1977 | Ellis | 128/421 |
| 4,289,135 | 9/1981 | Nordenstrom et al. | 128/419 R |
| 4,313,438 | 2/1982 | Greatbatch | 128/419 F |
| 4,314,554 | 2/1982 | Greatbatch | 128/419 F |

FOREIGN PATENT DOCUMENTS

| | | |
|---|---|---|
| 1589021 | 9/1969 | Fed. Rep. of Germany . |
| 2558525 | 8/1976 | Fed. Rep. of Germany . |
| 22035805 | 11/1978 | United Kingdom . |
| 2123698 | 2/1984 | United Kingdom . |
| 2181059 A | 4/1987 | United Kingdom . |

Primary Examiner—Lee S. Cohen
Assistant Examiner—Scott Getzow
Attorney, Agent, or Firm—Frishauf, Holtz, Goodman & Woodward

[57] ABSTRACT

Apparatus for supplying electric energy to biological tissue with a view to supporting different physiological processes, including different phases of healing, growth, modification og pathological states, for example deterioration in blood flow, chronic pain, fluid accumulation in tissue etc., and similarly with a view to influencing viability conditions of, for instance, tumor tissue, the apparatus essentially comprising at least two electrodes connected to a voltage source. One electrode is adapted to be disposed in or on the biological tissue which is to be supported in its physiological or pathophysiological cycle, and the other electrode is adapted to be disposed in spaced-apart relationship from the biological tissue in such a position that electrically conducting circuits exist between the electrodes, the voltage source being arrnaged, via said electrodes, to supply current through the biological tissue.

For simulating the physiological healing process, a controller is connected to the voltage source to supply a current whose amplitude values alternate with time, and each maximum amplitude value is lower in absolute terms than the immediately preceding amplitude value. The alternation of the current is caused to take place several times.

22 Claims, 1 Drawing Sheet

METHOD AND APPARATUS FOR SUPPLYING ELECTRIC ENERGY TO BIOLOGICAL TISSUE FOR SIMULATING THE PHYSIOLOGICAL HEALING PROCESS

BACKGROUND OF THE INVENTION

The present invention relates to an apparatus for supplying electric energy to biological tissue with a view to supporting different physiological processes, including various phases of healing, growth, modification of pathological states, for example deterioration in blood flow, chronic pain, fluid accumulation in tissue etc., and similarly with the view to influencing viability conditions of, for instance, tumour tissue, the apparatus essentially comprising at least two electrodes connected to a D.C. voltage source, of which one electrode is intended to be disposed in or on the bio-tissue which is to be supported in its physiological or patho-physiological cycle, and the other electrode is intended to be disposed in spaced-apart relationship from the biological tissue in such a position that electrically conductive circuits exist between said electrodes, the voltage source being arranged, via said electrodes, to supply current through the biotissue.

BACKGROUND ART

It is previously known in this art that power may be supplied to biological tissue by the intermediary of electrodes of different designs, in or outside that tissue portion which is to be treated. In this prior-art case, the electrodes are connected to a specially designed current emitter. This current emitter, known int. al. from Swedish patent No. 7812092-0 (corresponding to U.S. Pat. No. 4,289,135), is described as being employed for destruction of tumour tissue.

Diathermy instrumentation may also be employed with great power input at high frequencies for obtaining tissue coagulation by heat.

Methods are also known for so-called stimulation of fracture healing across implanted electrodes, as well as the application of electromagnetic, constant or variable fields from Helmholt's loops outside fractures. These prior-art methods have, as far as is known, not been based on the physiological requirements of tissue for healing, which, in crucial aspects, have hitherto been unknown.

OBJECT AND SUMMARY OF THE INVENTION

The primary object of the present invention is to propose an apparatus, by means of which the current emission may be adapted to the varying physiological and pathological reaction conditions of the tissue for attaining a good treatment result.

The apparatus as described by way of introduction— for attaining the above-indicated object—has been designed such that the above-mentioned voltage source, for simulating the physiological healing process, supplies a current whose amplitude value alternates with time, that each maximum amplitude value is lower in absolute terms than the amplitude value immediately preceding in time, and that the above-mentioned alternation of the current is caused to be effected a plurality of times.

BRIEF DESCRIPTION OF THE DRAWINGS

The nature of the present invention and its aspects will be more readily understood from the following brief description of the accompanying Drawings, and discussion relating thereto.

DESCRIPTION OF PREFERRED EMBODIMENT

Figure 1:
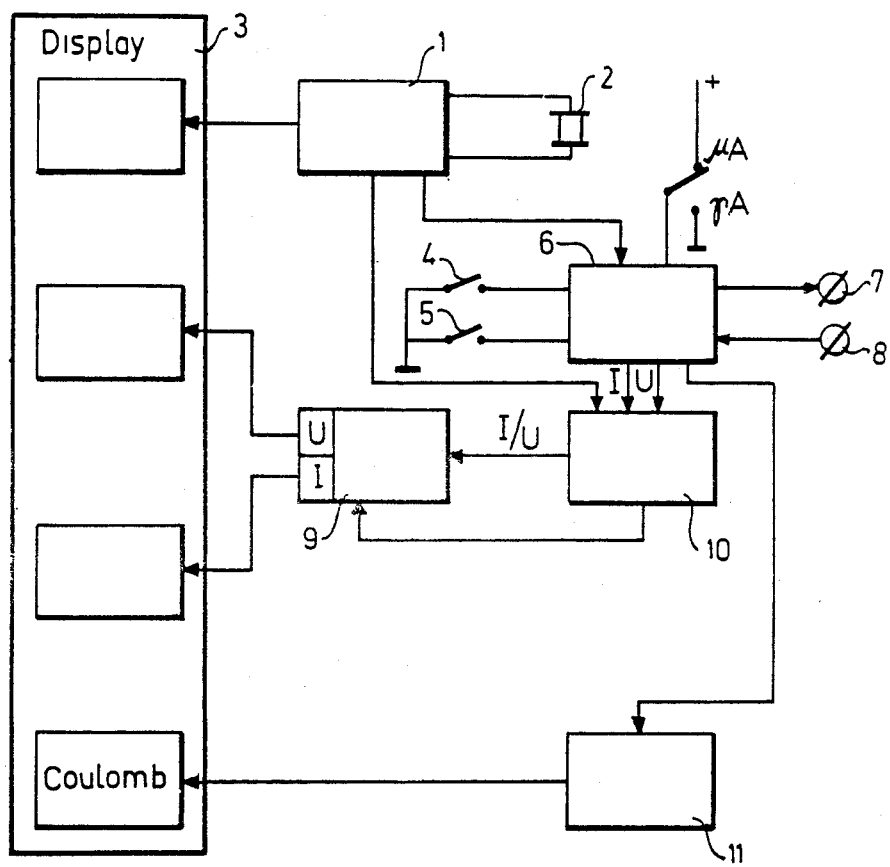
FIG. 1 is a block diagram of a suitable voltage source selected for means of exemplification.

Referring to the Drawings, the embodiment of the present invention is based—as opposed to existing treatment apparatuses— on the varying requirements of support or modification of electric power supply as required in different pathological states. These requirements, which must be plotted before different treatments, may then be employed in the present invention, which, in one embodiment, may be programmed for different functions. By giving these functions a wide programming possibility, the present invention may be utilized for several states, for example fracture or wound healing, rheumatic arthritis, glaucoma, healing of tumour tissue etc.

The present invention, which is based on the inventor's many years' practical experiments and treatment of patients suffering from cancer, may cite fracture healing as a prototype for the support of tissue healing, which, fundamentally, always appears to take place according to the major principle on which the present invention is based.

According to this major principle, there will occur in each fracture or other tissue damage, a spontaneous degradation of tissue which gives rise to electrochemical polarization of the damaged tissue in relation to its undamaged surroundings. This polarization is initially electropositive of the order of magnitude of a few hundred millivolts and constitutes the electromotoric power in an electrogenic transport system for tissue material. This major principle has recently been employed by the inventor in the case described in detail and experimentally tested in vitro, in vivo on animals and in vivo on human patients.

This major principle includes new, previously unknown facts, for example a new function of the blood vessels, whose walls have a high degree of resistivity in relation to the conductive media, namely blood plasma. The blood vessels have an electric transmission by the intermediary of the blood capillaries, which contract segmentally under the action of the superposed electromotoric field. Hereby, ion transports are shut in ion channels through the endothel cells of the blood capillaries and the leaking stomata therebetween. Hence, influence by diffusion, pressure differences and differences in osmotic pressure across the capillaries and the effect of gravitation will be excluded. The superposed electric gradient can, on the other hand, induce electron transfer across the endothel cells via globular proteins in a manner which was first demonstrated by Peter Mitchell in inner mitochondria membranes and is here shown to be present in the membranes of the endothel cells. There will thereby be obtained, on electron transfers, a biological equivalent to the electrode reactions in electrophoresis. As a result, the electromotoric power which is generated in the injury can drive ions in the blood vessels and in the interstitial, conductive tissue liquid. This is the basis of the material transport which is induced by the injury on healing.

This transport system permits accumulation of electronegative ions and repulsion of electropositive ions during the electropositive phase of the tissue damage. In a later phase, the damage converts to becoming electronegative in relation to its surroundings. In the particular current transport system which has been identified and plotted, the current transport reverts, therefore, so that electropositive ions are accumulated and electronegative ions are repulsed from the damage. This cycle is characterized by a fluctuating, attenuating potential difference to the immediate surroundings which may be utilized according to the present invention. Every tissue injury requires, for its healing, both anions and cations, but these must be employed in determined sequences. The total current transport is of crucial importance. This is calculated on the basis of determination of the size of the tissue damage. A direct relationship has been demonstrated between the total quantity of energy which is released in an injury and the quantity of current transport this energy can deliver for healing the damage. In simple terms, the injury itself will, in a normal healing process, deliver that energy which is required for healing the damage.

If the tissue damage were solely electropositive, only anions would be accumulated therein, while cations would be repulsed thence. For natural reasons, both anions and cations are needed in the healing process. In animal experiments, it has been demonstrated that the damage potential slowly fluctuates with time. For a given injury, the ion transports must, therefore, be influenced, int. al., by the conductive properties of surrounding tissue. In good conductivity, a given electromotoric force may, in a short time, transport a sufficient quantity of ions both during the positive and the negative phase of the injury, i.e. rapidly heal the injury. In poor conductivity, these transports take longer time and may need to be supported by a variable current source. An applicable fluctuation pattern in fracture healing has been studied experimentally on rodent fractures, this pattern giving polarity, voltage and current force, respectively, for the transports during the requisite healing time for an injury of a given size.

None-invasive methods, for example X-ray, computer tomography and magnetic resonance may be utilized for determining the size of the injury before treatment. Since the degradation of a small injury releases energy which gives voltage changes equivalent to a large injury, it is possible, by means of size determination, to calculate the quantity of ion transport in the different phases which is required for healing the injury. This may be effected by either calculating and adapting the current time integral the invention is to give or by sensing the actual current passage of the invention and allowing the voltage to rise to a level which permits adequate transport of ions in suitable phases during a predetermined time.

With the above disclosures as a background, the present invention enjoys the following properties. Using an electric battery which is preferably rechargeable but is separable during use from the mains power supply, varying voltage and current force can drive ions to and from the fracture with the application of both electropositive and electronegative phase of the injury. In one embodiment, there is a possibility of applying a satisfactorily positive voltage in order, during a reasonable time, to accumulate a sufficient quantity of anions. On approaching the calculated current figure for anion accumulation, after the preceding determination of the size of the injury, the current through-flow levels out towards the zero value during a time of from 0.1 to 10 days, preferably approximately one week, whereafter the desired negative phase commences for inverting or alternation of the current. By such means, the flow time integral will be programmed in a corresponding manner to the positive. Thereafter, the voltage fluctuations, the varying voltage, are attenuated, until clinical stability is achieved in the fracture, in other words until the injury is substantially healed.

A voltage source selected by way of example as being suited for reducing the present invention into practice is illustrated in the block diagram according to FIG. 1. This D.C. voltage source preferably includes a block 12 which generally designates mains chargeable accumulators or batteries (not shown in detail on the drawing). This disconnection from the mains is to be preferred in order to avoid the risk that disturbances, transient voltages etc. deriving from the mains power affect the D.C. voltage source.

The D.C. voltage source includes a clock 1 suitably controlled by a crystal 2, the clock being arranged to control the process. The real time measured by the clock 1 is shown on a display 3 of suitable type. The clock 1 operates, by the intermediary of, for example, a relay (not shown in detail), two tongues 4 and 5 for acting on a current generator 6 to increase or reduce the current emitted from two patient connections 7 and 8, the current being, by the intermediary of electrodes (not shown on the Drawings), surgically implanted into the tissue portions which are to be treated, supplied to the biological tissue whose physiological cycle is to be supported.

As a complement or alternative to the crystal-controlled clock 1, equipment (not shown) for controlling the process may naturally be provided for programming, by means of which previously obtained experience values, limits etc.—as well as values revealed or sensed from the treatment—may be caused to act upon the initial values generated from the current generator 6 in respect of current, voltage, time alternation of current, degree of modification etc., in an appropriate manner. This refers in particular to those cases where it is possible relatively instantaneously to sense the result of the healing process and thereby establish more or less exactly when the next phase in the healing process is to be introduced by alternation of the current.

The D.C. voltage source further includes a meter 9 for continuously or instantaneously reading off the actual voltage and current which are retrieved by the intermediary of a switch device 10 from the current generator 6 and are shown on the display 3. A charging meter 11 is continuously connected to the current generator 6 and its value is also shown on the display 3. This charging meter 11 is, in this context, essential, since—as was mentioned above—the volume of charge which is to be supplied to damaged tissue is directly related to the volume of the injury itself. By manual means, the current supply is reduced to zero when sufficient charging volume has been supplied to the treatment site. If—on the other hand—equipment for programming is employed, a preprogrammed charging volume may be compared with the charging volume supplied to the connections 7 and 8, and when these values are equal, the current is reduced to zero and/or the current supply is alternated automatically from the current generator 6.

As a complement or alternative, it is further conceivable—before the current supply from the current generator is commenced—to utilize the electrodes implanted in the biological tissue for sensing the current direction of the physiological healing process and adapt the emission current direction generated from the current generator 6 in response thereto.

However, as a rule, it is most appropriate to commence the treatment from the beginning, corresponding to the onset of a natural healing process, with the current directed from the injured tissue.

Through the above-mentioned increase and decrease, respectively, of the current from the current generator 6 controlled by the clock 1 via relays, there will be obtained a time-controlled stepwise increase and reduction of the current, but, naturally, it is also possible to continually increase and reduce the current by suitable means.

Figure 2:
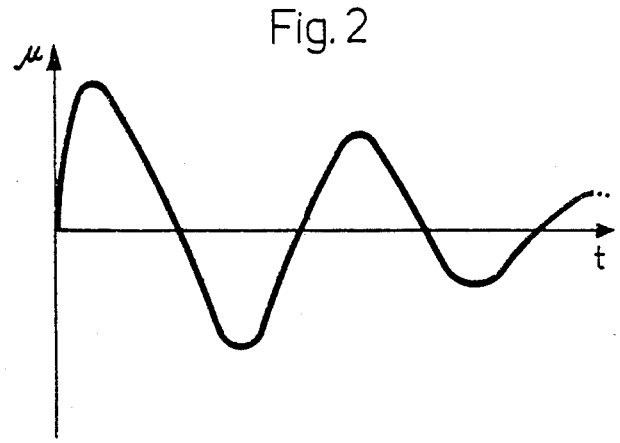
FIG. 2 is a diagram showing the voltage as a function of time.

FIG. 2 illustrates the potential which is impressed by the current generator 6 across the connections 7 and 8 as a function of time, since the voltage is simpler to follow than the essentially corresponding variations of the current (in reasonably constant resistivity of the biological tissue). The time axis T in the diagram here embraces approx. 3–4 weeks and—as will be apparent from the curve—is damped asymptotically towards zero at the end of this time interval. The initial current application up to the first maximum takes place within a few seconds up to a few minutes, while, on the other hand, the change thence to zero takes place stepwise or continually for a long time from 0.1 to 2 days up to 7–10 days and continued alternation of the current to the negative maximum and then further to zero takes place within approximately the same time interval as above, i.e. the distance between two mutually subsequent alternation points (when the current or voltage is, as a rule, but not necessarily, zero), is approx. 7 days. The current to the electrode connections 7 and 8 hence alternates extremely slowly. After 3–4 alternations of the current direction, healing will have essentially taken place, on condition that the total volume of charge which is supplied to the tissue substantially corresponds to the volume of the damage.

The present invention should not be considered as restricted to that described above and shown on the drawings, many modifications being conceivable without departing from the spirit and scope of the appended claims.

What I claim and desire to secure by letters patent is:

1. Apparatus for supplying electric energy to biological tissue for supporting different physiological processes and for influencing viability conditions, comprising;
   at least two electrodes, a first of said at least two electrodes being adapted to be disposed in or on the biological tissue which is to be supported in a physiological or pathophysiological cycle, and a second of said at least two electrodes being adapted to be disposed in spaced-apart relationship from said first of said at least two electrodes the biological tissue in such a position that electrically conducting circuits exist between said at least two electrodes;
   a voltage source coupled to said at least two electrodes for supplying electric current through said biological tissue; and
   control means coupled to said voltage source for supplying to said electrodes a current whose amplitude values alternate with time for simulating a physiological healing process, said current having successive maximum amplitude values such that each maximum amplitude value of said current is lower in absolute terms than the immediately preceding maximum amplitude value; and
   said control means causing said alternation of said current to take place a plurality of times within a cycle time interval which lies between 0.1 and 10 days.

2. The apparatus of claim 1, wherein said time interval lies between 0.1 and about 7 days.

3. The apparatus of claim 1, wherein:
   said control means supplies said current through said electrodes in a form which is integrated in time, such that the total of the integrated magnitudes of the current is preselected in relation to the volume of the biological tissue which is to be supported; and
   said control means including means for automatically disconnecting said current when said integrated total has been achieved.

4. The apparatus of claim 3, further comprising sensing means for sensing the result of the simulated physiological healing process, and wherein said control means is operable responsive to the results sensed by said sensing means to change each respective point of time for alternation of the current.

5. The apparatus of claim 4, wherein:
   said control means controls said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;
   and said control means further changing said current from said first mentioned negative maximum amplitude value, during a period of several days, to a zero value and then to a new maximum positive amplitude value which, in absolute terms, is lower than the immediately preceding negative maximum amplitude value; and
   said control means causes the above alternation cycle to be repeated until the desired physiological process result has been achieved.

6. The apparatus of claim 1, further comprising sensing means for sensing the result of the simulated physiological healing process, and wherein said control means is operable responsive to the results sensed by said sensing means to change each respective point of time for alternation of the current.

7. The apparatus of claim 6, wherein:
   said control means controls said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;
   and said control means further changing said current from said first mentioned negative maximum amplitude value, during a period of several days, to a zero value and then to a new maximum positive amplitude value which, in absolute terms, is lower than the immediately preceding negative maximum amplitude value; and said control means causes the above alternation cycle to be repeated until the desired physiological process result has been achieved.

8. The apparatus of claim 1, wherein:

said control means controls said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;

and said control means further changing said current from said first mentioned negative maximum amplitude value, during a period of several days, to a zero value and then to a new maximum positive amplitude value which, in absolute terms, is lower than the immediately preceding negative maximum amplitude value; and said control means causes the above alternation cycle to be repeated until the desired physiological process result has been achieved.

9. The apparatus of claim 1, further comprising programming means for preprogramming at least prior experience values, and processing present sensed values; and wherein said control means is operable responsive to values in said programming means.

10. The apparatus of claim 1, wherein said control means controls the current in said electrodes to first flow in one direction from one electrode to the other.

11. The apparatus of claim 1, wherein said control means controls the current in said electrodes so that the current is first brought into phase with a current direction of a physiological healing process.

12. A method for supplying electric energy to biological tissue for supporting different physiological processes and for influencing viability conditions, comprising;

disposing a first electrode of at least two electrodes in or on the biological tissue which is to be supported in a physiological or pathophysiological cycle, and disposing a second electrode of said at least two electrodes in spaced-apart relationship from said first electrode on said biological tissue in such a position that electrically conducting circuits exist between said at least two electrodes;

supplying electrical power to said at least two electrodes for supplying electric current through said electrodes and through said biological tissue; and controlling said supplied electric current so as to having amplitude values alternate with time for simulating a physiological healing process, said supplied electric current having successive maximum amplitude values such that each maximum amplitude value of said electric current is lower in absolute terms than the immediately preceding maximum amplitude value; and causing said alternation of said electric current to take place a plurality of times within a cycle time interval which lies between 0.1 and 10 days.

13. The method of claim 12, wherein said time interval lies between 0.1 and about 7 days.

14. The method of claim 12, further comprising controlling said supplied current so as to be in a form which is integrated in time, and such that the total of the integrated magnitudes of the current is preselected in relation to the volume of the biological tissue which is to be supported; and automatically disconnecting said current when said integrated total has been achieved.

15. The method of claim 14, further comprising sensing the result of the simulated physiological healing process, and controlling said supplied current responsive to the results of said sensing to change each respective point of time for alternation of the current.

16. The method of claim 15, further comprising:

controlling said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;

and further changing said current from said first mentioned negative maximum amplitude value, during a period of several days, to a zero value and then to a new maximum positive amplitude value which, in absolute terms, is lower than the immediately preceding negative maximum amplitude value; and causing the above alternation cycle to be repeated until the desired physiological process result has been achieved.

17. The method of claim 12, further comprising sensing the result of the simulated physiological healing process, and controlling said supplied current responsive to the results of said sensing to change each respective point of time for alternation of the current.

18. The method of claim 17, further comprising:

controlling said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;

and further changing said current from said first mentioned negative maximum amplitude value, during a period of several days, to a zero value and then to a new maximum positive amplitude value which, in absolute terms, is lower than the immediately preceding negative maximum amplitude value; and causing the above alternation cycle to be repeated until the desired physiological process result has been achieved.

19. The method of claim 12, further comprising:

controlling said alternation of said current from said voltage source slowly, either continually or stepwise, to change from an amplitude value equal to zero to a maximum amplitude value, and thereafter and during several days, to decline to zero and alternate to a negative maximum amplitude value which is, in absolute terms, less than the immediately preceding maximum amplitude value;

and further changing said current from said first mentioned negative maximum amplitude value, during a period of several days, to a zero value and then to a new maximum positive amplitude value which, in absolute terms, is lower than the immediately preceding negative maximum amplitude value; and causing the above alternation cycle to be repeated until the desired physiological process result has been achieved.

20. The method of claim 12, further comprising preprogramming at least prior experience values, and processing present sensed values; and controlling said current responsive to said preprogrammed values.

21. The apparatus of claim 12, further comprising controlling the current in said electrodes to first flow in one direction from one electrode to the other.

22. The method of claim 12, further comprising controlling the current in said electrodes so that the current is first brought into phase with a current direction of a physiological healing process.

* * * * *